United States Patent [19]

Waldvogel

[11] Patent Number: 5,061,245
[45] Date of Patent: Oct. 29, 1991

[54] ARTERIAL BYPASS TOOL

[76] Inventor: Chester W. Waldvogel, Rte. 1, Box 224 D, Queenstown, Md. 21658

[21] Appl. No.: 467,567

[22] Filed: Jan. 19, 1990

[51] Int. Cl.$^5$ .............................................. A61M 5/178
[52] U.S. Cl. ........................................ 604/170; 623/1
[58] Field of Search ................... 604/8, 158, 164, 170; 623/1, 12; 600/36; 606/153, 155, 108, 129, 148; 128/898

[56] References Cited

U.S. PATENT DOCUMENTS

| | | |
|---|---|---|
| 2,024,982 | 12/1935 | Scott . |
| 2,118,631 | 5/1938 | Wappler .............................. 604/170 |
| 2,221,138 | 11/1940 | Hendrickson . |
| 2,458,305 | 1/1949 | Sanders ............................... 604/170 |
| 2,905,178 | 9/1959 | Hilzinger . |
| 3,316,913 | 5/1967 | Swenson . |
| 3,710,777 | 1/1973 | Sparks .................................... 623/1 |
| 3,866,247 | 2/1975 | Sparks .................................... 623/1 |
| 4,774,949 | 10/1988 | Fogarty . |

*Primary Examiner*—C. Fred Rosenbaum
*Assistant Examiner*—William W. Lewis
*Attorney, Agent, or Firm*—Jerry T. Kearns

[57] ABSTRACT

An arterial bypass tool for use in inserting and positioning a bypass artery alongside an occluded artery within the body of a patient includes an arcuate tubular sheath. A rod is slidably received through the sheath and terminates at a forward end in a tapering, radiused tip. A rearward end of the rod terminates in an enlarged tab dimensioned for passage through the sheath. A pair of apertures formed in the tab allow a bypass artery to be stitched thereto. In use, an entrance incision is formed in a patient adjacent one end of an occluded artery. The radiused tip is inserted through the entrance incision and the sheath and enclosed rod are passed alongside the occluded artery. An exit incision is then formed adjacent the radiused tip. The forward end of the sheath is then pushed through the exit incision. A bypass artery is secured to the tab at the opposite end of the rod, adjacent the entrance incision. The rod is then pulled through the sheath, leaving the bypass artery disposed within the sheath, alongside the occluded artery. The bypass artery is then detached from the tab, and the sheath is removed from the patient, while the bypass artery is held in place. The end portions of the bypass artery are then connected to bypass the occluded artery, and the entrance and exit incisions are closed. The procedure allows a bypass operation to be performed with a minimum number of stitches, resulting in a rapid patient recovery.

20 Claims, 3 Drawing Sheets

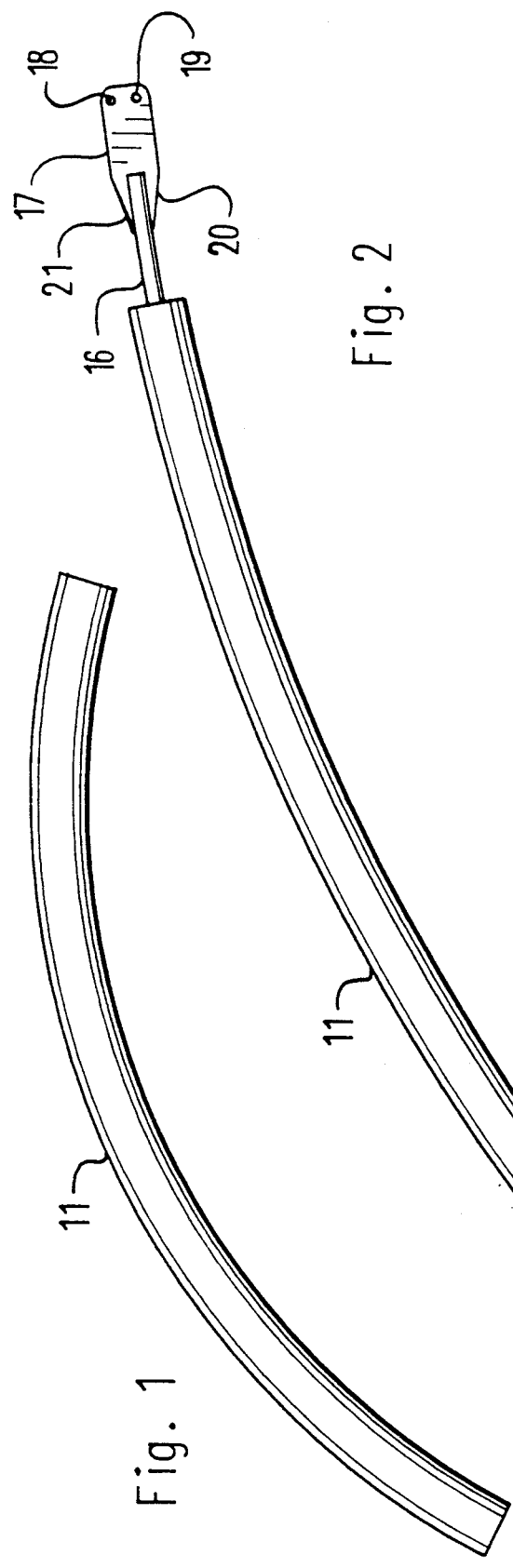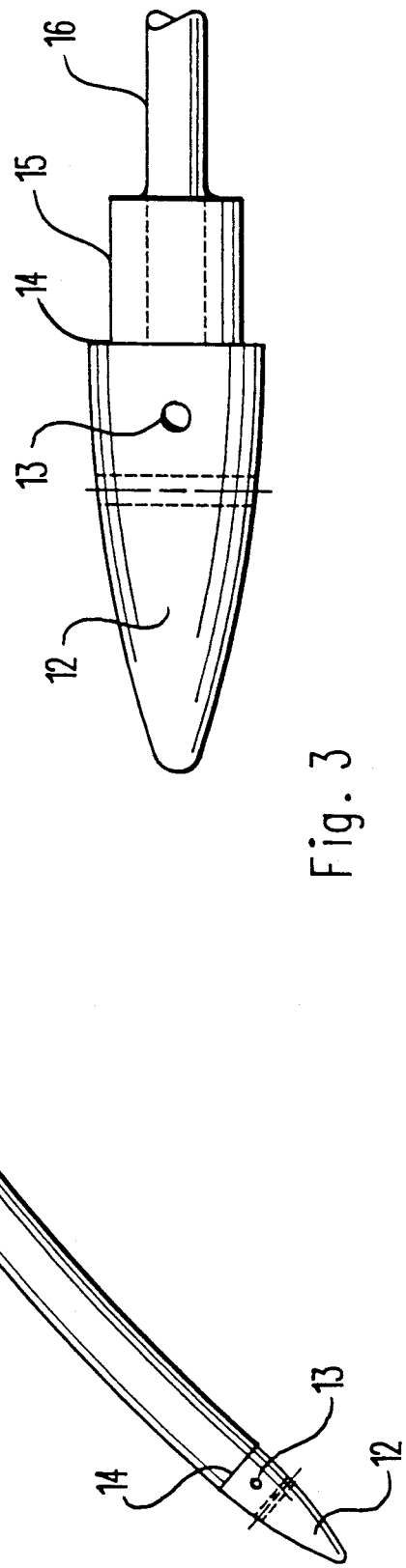

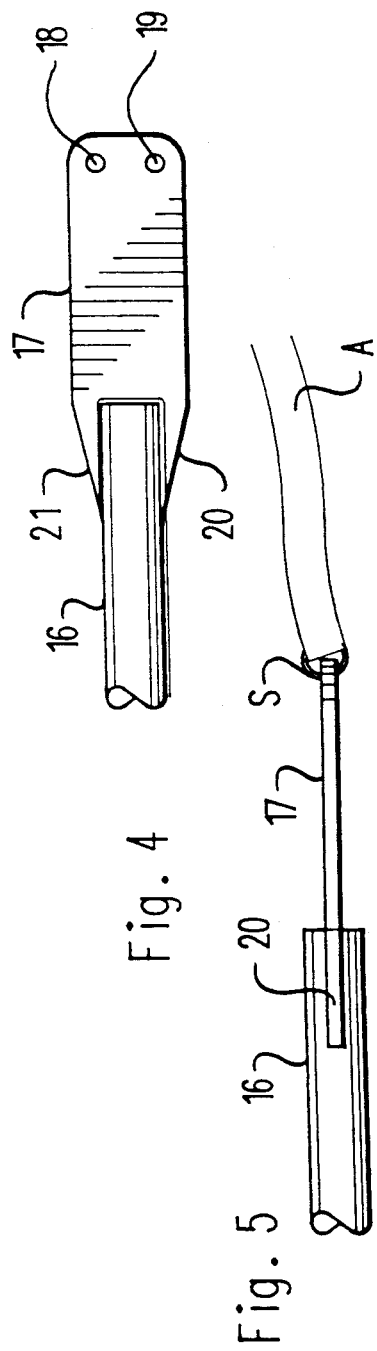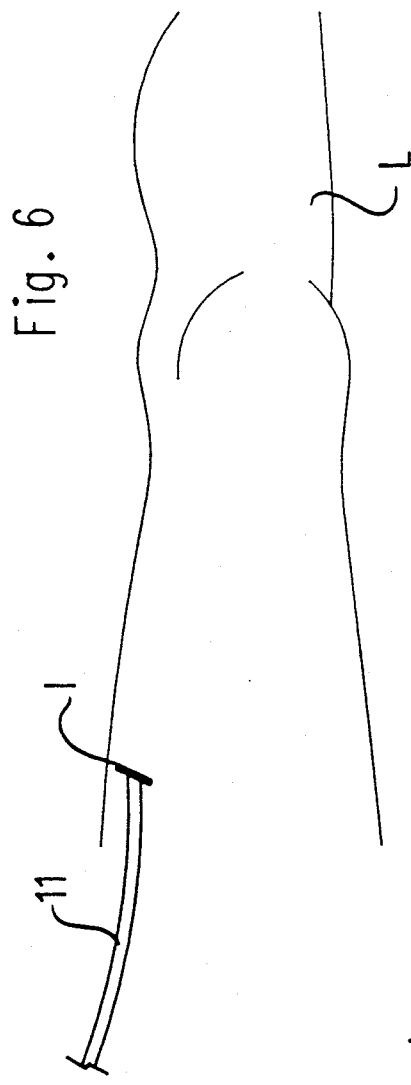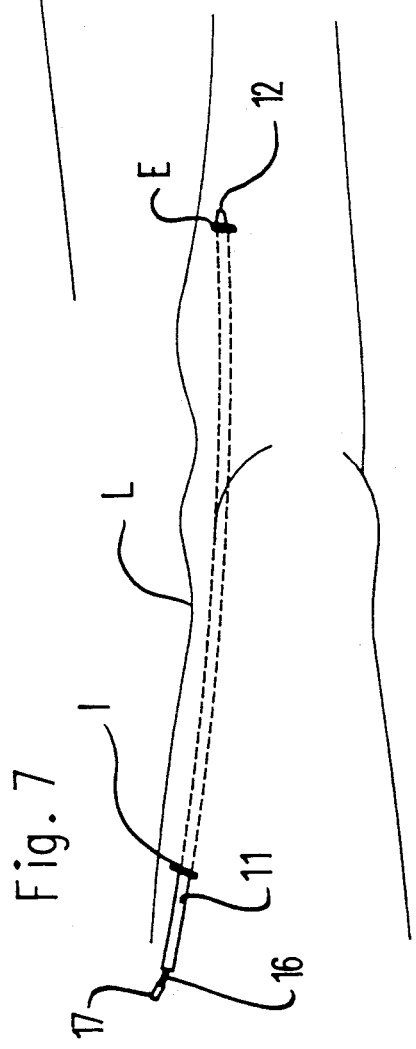

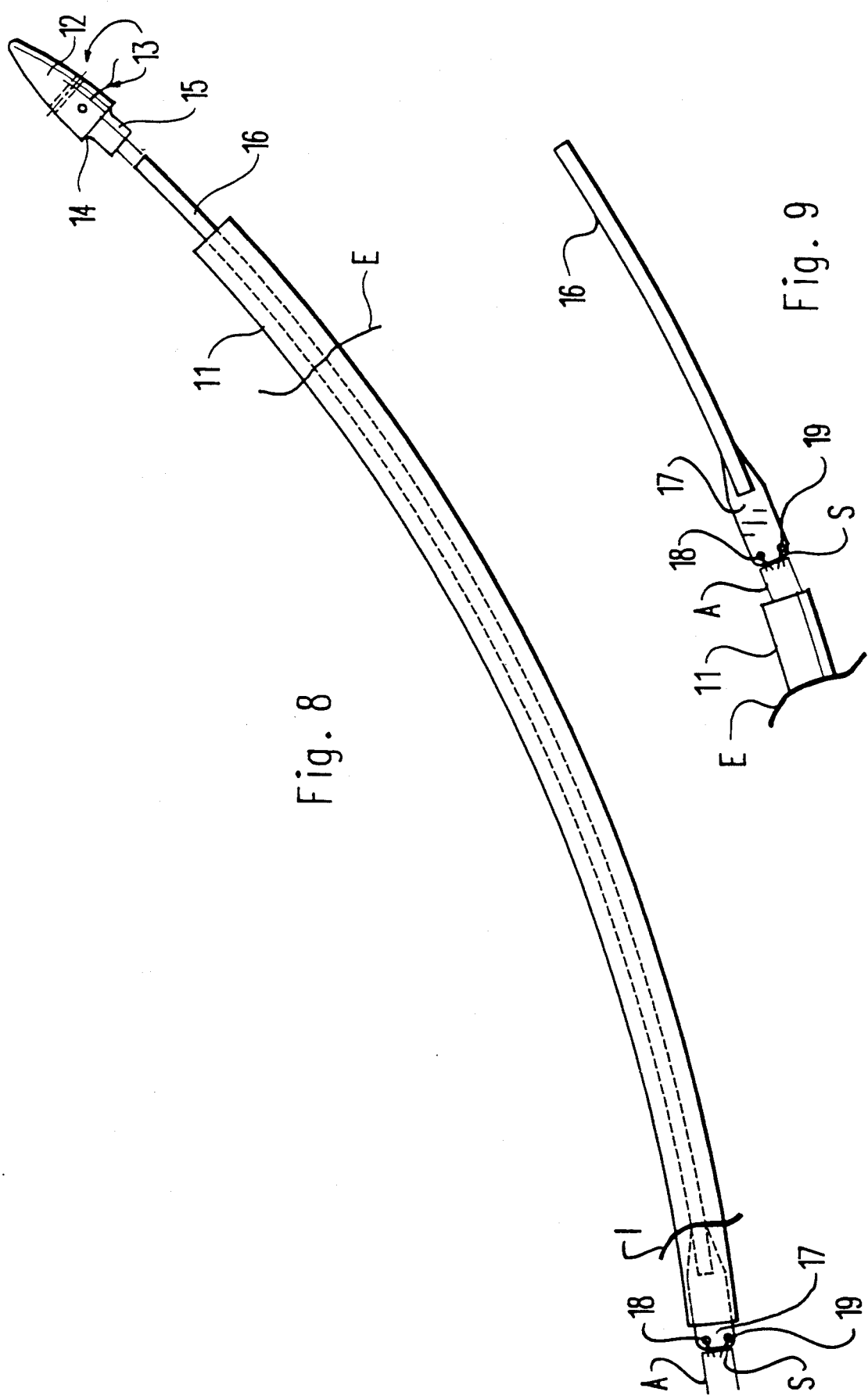

5,061,245

ARTERIAL BYPASS TOOL

BACKGROUND OF THE INVENTION

1. Field of the Invention

The present invention relates to surgical tools, and more particularly pertains to an improved arterial bypass tool for use by vascular surgeons performing arterial bypass operations. The conventional method of performing a bypass operation to replace an occluded artery in the leg of a patient requires an incision to be made along the entire length of the occluded artery. This invasive procedure requires as many as 300 stitches and increases the possibility of infection and other complications which prolong patient recovering. In order to overcome this problem, the present invention provides an arterial bypass tool which allows a bypass operation to be performed utilizing only small entrance and exit incisions. This results in a reduction of the stitches required to approximately to 16 to 20, resulting in a reduction of complications and an appreciably expedited recovery. Additionally, the arterial bypass tool and procedure of the present invention allow a great reduction in the operating time and resultant medical expenses.

2. Description of the Prior Art

Various types of surgical tools are known in the prior art. A typical example of such a surgical tool is to be found in U.S. Pat. No. 2,024,982, which issued to H. Scott on Dec. 17, 1935. This patent discloses a urethral catheter which includes a tubular sheath through which an elongated insertion member is passed. The insertion member terminates in a radiused tapered tip which is entirely insertable within the tubular sheath. U.S. Pat. No. 2,221,138, which issued to F. Hendrickson on Nov. 12, 1940, discloses a filiform guide for use in exploring and treating strictures in various body organs. U.S. Pat. No. 2,905,178, which issued to P. Hilzinger on Sept. 22, 1959, discloses a surgical control device for controlling a surgical implement within a body passage. The device includes a bendable tubular guide having a control member insertable therethrough. U.S. Pat. No. 3,316,913, which issued to R. Swenson on May 2, 1967, discloses a catheter guiding forceps for controlling movement of a tubular catheter within the trachea of a patient. U.S. Pat. No. 4,774,949, which issued to T. Fogarty on Oct. 4, 1988, discloses a catheter having a lumen which extends along most of the length catheter and then curves outwardly to terminate in a port for the passage of guide wires and catheters through the lumen into branch arteries. The device is designed for surgical procedures for diagnosing and treating occluded arteries.

While the above mentioned devices are directed to surgical tools, none of these devices disclose an arterial bypass tool and method of use for performing an arterial bypass operation utilizing only small entrance and exit incisions. Inasmuch as the art is relatively crowded with respect to these various types of surgical tools, it can be appreciated that there is a continuing need for and interest in improvements to such surgical tools, and in this respect, the present invention addresses this need and interest.

SUMMARY OF THE INVENTION

In view of the foregoing disadvantages inherent in the known types of surgical tools now present in the prior art, the present invention provides an improved arterial bypass tool. As such, the general purpose of the present invention, which will be described subsequently in greater detail, is to provide a new and improved arterial bypass tool which has all the advantages of the prior art surgical tools and none of the disadvantages.

To attain this, a representative embodiment of the concepts of the present invention is illustrated in the drawings and makes use of an arterial bypass tool for use in inserting and positioning a bypass artery alongside an occluded artery within the body of a patient which includes an arcuate tubular sheath. A rod is slidably received through the sheath and terminates at a forward end in a tapering, radiused tip. A rearward end of the rod terminates in an enlarged tab dimensioned for passage through the sheath. A pair of apertures formed in the tab allow a bypass artery to be stitched thereto. In use, an entrance incision is formed in a patient adjacent one end of an occluded artery. The radiused tip is inserted through the entrance incision and the sheath and enclosed rod are passed alongside the occluded artery. An exit incision is then formed adjacent the radiused tip. The forward end of the sheath is then pushed through the exit incision. A bypass artery is secured to the tab at the opposite end of the rod, adjacent the entrance incision. The rod is then pulled through the sheath, leaving the bypass artery disposed within the sheath, alongside the occluded artery. The bypass artery is then detached from the tab, and the sheath is removed from the patient, while the bypass artery is held in place. The end portions of the bypass artery are then connected to bypass the occluded artery, and the entrance and exit incisions are closed. The procedure allows a bypass operation to be performed with a minimum number of stitches resulting in a rapid patient recovery.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the public generally, and especially those who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved arterial bypass tool which has all the advantages of the prior art surgical tools and none of the disadvantages.

It is another object of the present invention to provide a new and improved arterial bypass tool which may be easily and efficiently manufactured and marketed.

It is a further object of the present invention to provide a new and improved arterial bypass tool which is of a durable and reliable construction.

An even further object of the present invention is to provide a new and improved arterial bypass tool which is susceptible of a low cost of manufacture with regard to both materials and labor, and which accordingly is then susceptible of low prices of sale to the consuming public, thereby making such surgical tools economically available to the buying public.

Still yet another object of the present invention is to provide a new and improved arterial bypass tool which provides in the apparatuses and methods of the prior art some of the advantages thereof, while simultaneously overcoming some of the disadvantages normally associated therewith.

Still another object of the present invention is to provide a new and improved arterial bypass tool which allows the performance of an arterial bypass operation in a relatively non-invasive manner.

Yet another object of the present invention is to provide a new and improved arterial bypass tool which enables an arterial bypass operation to be performed utilizing only small entrance and exit incisions.

Even still another object of the present invention is to provide a new and improved arterial bypass tool which allows arterial bypass operations to be performed in less time and with a reduced patient recovery time.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a plan view illustrating the tubular sheath portion of the bypass tool according to the present invention.

FIG. 2 is a plan view illustrating the entire assembled bypass tool.

FIG. 3 is a detail view, illustrating the construction of the radiused, tapered insertion tip.

FIG. 4 is a detail view illustrating the construction of the bypass artery attachment tab.

FIG. 5 is a side view illustrating the manner of use of the bypass tool of the present invention.

FIG. 6 is a diagrammatic illustration of a bypass operation performed utilizing the tool of the present invention.

FIG. 7 is a diagrammatic view further illustrating the performance of a bypass operation according to the present invention.

FIG. 8 is an additional diagrammatic view, further illustrating the manner of use of the arterial bypass tool of the present invention.

FIG. 9 illustrates an additional step in an arterial bypass operation performed according to the present invention.

DESCRIPTION OF THE PREFERRED EMBODIMENT

With reference now to the drawings, and in particular to FIG. 1 thereof, a new and improved arterial bypass tool embodying the principles and concepts of the present invention will be described.

More specifically, it will be noted that the first embodiment of the invention includes an arcuate tubular sheath 11.

As shown in FIG. 2, a rod 16 is slidably received through the sheath 11. A tapering radiused, generally bullet-shaped tip 12 is secured to a forward end of the rod 16 by a transverse pin 13. An annular shoulder or ledge 14 of the tip 12 is in abutment with the forward end face of the sheath 11. The rearward end of the rod 16 is provided with a longitudinal slot in which a forward end of a tab 17 is secured. The tab 17 has tapering forward side wall portions 20 and 21 to facilitate passage of the tab 17 to the sheath 11. A pair of apertures 18 and 19 are formed through the trailing end of the tab 17 and are utilized to secure a bypass artery. The forward end of the bypass artery is stitched to the tab 17, through the apertures 18 and 19.

As illustrated in FIG. 3, the tip 12 has a rearwardly directed reduced diameter cylindrical shank 15, which forms the annular shoulder or ledge 14. A cylindrical bore is centrally formed in the shank 15 and receives the forward end portion of the rod 16, which is brazed to the shank 15.

FIG. 4 is an enlarged view illustrating the tab 17 secured, for example by brazing, to the rearward end of the rod 16.

As shown in FIG. 5, a forward end of a bypass artery A may be secured by sutures S to the trailing end of the tab 17. The tab 17 has a flat, generally rectangular configuration and is secured in a longitudinal slot formed in the rearward end of the rod 16.

FIG. 6 illustrates an initial step in the performance of an arterial bypass operation in the leg L of a patient. A small entrance incision I is formed adjacent one end of an occluded artery. The radiused tip portion 12 of the tool illustrated in FIG. 2 is inserted through the entrance incision I. The tubular sheath is then pushed through the leg L of the patient, alongside the occluded artery. The leg must be initially oriented at a 29 inch radius, to match the curvature of the sheath 11.

As shown in FIG. 7, an exit incision E is then formed adjacent an opposite end of the occluded artery, and the radiused tip 12 is passed therethrough.

As shown in FIG. 8, the forward end portion of the sheath 11 is also pushed through the exit incision E. The forward end of the bypass artery A is secured by sutures S through the apertures 18 and 19 provided in the trailing end of the tab 17.

As shown in FIG. 9, the rod 16 is pulled entirely through the tubular sheath 11, and out of the exit incision E, while the sheath 11 is held in place. The forward end of the bypass artery A is then detached from the tab 17, leaving the artery A disposed within the sheath 11, and alongside the occluded artery. The bypass artery A is then held adjacent one end, and the sheath 11 withdrawn from the patient's leg. The opposite ends of the artery A are then connected to bypass the occluded artery, and the entrance and exit incisions are closed. The procedure may be accomplished utilizing from 8 to 10 stitches to close each of the incisions.

While the use of the bypass tool of the present invention has been described with respect to a leg artery bypass, it should be noted that the tool, suitably dimensioned, may be utilized in various body parts. It is contemplated that the tool of the present invention may be provided as a set, to allow selection of a tool of appropriate dimensions, depending upon a surgical procedure to be performed. A preferred set consists of six tubular sheaths 11. A first three sheaths have a length of 24 inches and a radius of curvature of 29 inches. The three sheaths have respective diameters of 0.25, 0.375 and 0.5 inches, with respective wall thicknesses of 0.02, 0.049 and 0.049 inches. The remaining three sheaths each have a length of 10 inches and a radius of curvature of 9 inches. The second three sheaths have respective diameters of 0.25, 0.375 and 0.5 inches, with associated respective wall thicknesses of 0.02, 0.049 and 0.049 inches. A surgical stainless steel material is preferred, although the tool may be formed utilizing a disposable plastic material. The internal rod 16 may be formed from a stainless steel material having a diameter of about 0.125 inches. The securement tab 17 may additionally be formed from a stainless steel material having a thickness of about 0.032 inches. The indicated dimensions are intended to illustrate sample dimensions of a workable bypass tool. It should be noted that these dimensions may be varied, depending upon the intended surgical procedure, without departing from the scope of the present invention. While a stainless steel reusable material has been described, it is contemplated that a disposable set of bypass tools may be marketed in a sterile sealed container and designed for one time usage and subsequent disposal.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An arterial bypass tool, comprising:
   a tubular sheath having first and second ends;
   a rod slidably received through said sheath;
   a first end of said rod terminating in a tapering radiused tip exteriorly adjacent said first end of said sheath; and
   a second end of said rod terminating in an enlarged tab dimensioned for passage through said sheath, said tab possessing a trailing end provided with at least one aperture.

2. The arterial bypass tool of claim 1, wherein said sheath is arcuate.

3. The arterial bypass tool of claim 1, wherein said tab is generally rectangular and possesses a forward end which tapers in width.

4. The arterial bypass tool of claim 1, wherein a forward end of said tab is received in a slot formed in a second end of said rod.

5. The arterial bypass tool of claim 1, wherein said tapering radiused tip possesses a rearwardly directed reduced diameter cylindrical shank dimensioned for insertion into said sheath.

6. The arterial bypass tool of claim 5, wherein said shank forms an annular ledge dimensioned for abutment with an end face of said sheath.

7. The arterial bypass tool of claim 5, wherein said shank possesses a central bore dimensioned for insertion of said first end of said rod.

8. The arterial bypass tool of claim 1, wherein said sheath, said rod, said tab and said radiused tip each comprise a stainless steel material.

9. The arterial bypass tool of claim 1, wherein said sheath, said rod, said tab and said radiused tip each comprise a disposable plastic material.

10. The arterial bypass tool of claim 1, wherein said sheath possesses a radius curvature of about 29 inches and a length of about 24 inches.

11. The arterial bypass tool of claim 1, wherein said sheath possesses a radius curvature of about 9 inches and a length of about 10 inches.

12. The arterial bypass tool of claim 1, wherein said sheath possesses a diameter in the range of about 0.25 to 0.50 inches.

13. An arterial bypass tool, comprising:
   a tubular sheath having first and second ends;
   a rod slidably received through said sheath;
   a first end of said rod terminating in a tapering radiused tip exteriorly adjacent said first end of said sheath, said tapering radiused tip possessing a rearwardly directed reduced diameter substantially cylindrical shank dimensioned for insertion into said sheath; and
   a second end of said rod terminating in an enlarged tab dimensioned for passage through said sheath.

14. The arterial bypass tool of claim 13, wherein said shank forms an annular ledge dimensioned for abutment with an end face of said sheath.

15. The arterial bypass tool of claim 13, wherein said shank possesses a central bore dimensioned for insertion of said first end of said rod.

16. The arterial bypass tool of claim 13, wherein said sheath, said rod, said tab and said radiused tip each comprise a stainless steel material.

17. The arterial bypass tool of claim 13, wherein said sheath, said rod, said tab and said radiused tip each comprise a disposable plastic material.

18. The arterial bypass tool of claim 13, wherein said sheath is arcuate.

19. The arterial bypass tool of claim 13, wherein said tab is generally rectangular and has a forward end which tapers in width.

20. A method of performing an arterial bypass operation, comprising the steps of:
providing:
- a tubular sheath;
- a rod extending through said tubular sheath;
- a first end of said rod terminating in a radiused tip exteriorly adjacent a first end of said sheath;
- a second end of said rod terminating in an enlarged tab dimensioned;
- at least one aperture formed through a free end of said tab;

forming an entrance incision in a patient adjacent a first end of an occluded artery;

inserting said radiused tip end through said entrance incision;

inserting said sheath through said entrance incision along an exterior of the occluded artery;

forming an exit incision adjacent a second end of the occluded artery;

passing said radiused tip and first end of said sheath through said exit incision;

securing a bypass artery to said tab;

pulling said rod through said sheath to dispose said bypass artery within said sheath;

detaching said bypass artery from said tab; and removing said sheath while restraining said bypass artery, whereby said bypass artery lies along said occluded artery.

* * * * *